US010357225B2

(12) United States Patent
Rice et al.

(10) Patent No.: US 10,357,225 B2
(45) Date of Patent: Jul. 23, 2019

(54) ULTRASONIC TRANSDUCER ELECTRODE ASSEMBLY

(71) Applicant: VOLCANO CORPORATION, San Diego, CA (US)

(72) Inventors: Cheryl Rice, San Diego, CA (US); Dongjuan Chris Xi, San Marcos, CA (US)

(73) Assignee: VOLCANO CORPORATION, San Diego, CA (US)

( * ) Notice: Subject to any disclaimer, the term of this patent is extended or adjusted under 35 U.S.C. 154(b) by 0 days.

(21) Appl. No.: 15/965,385

(22) Filed: Apr. 27, 2018

(65) Prior Publication Data

US 2018/0242949 A1     Aug. 30, 2018

Related U.S. Application Data

(63) Continuation of application No. 15/094,717, filed on Apr. 8, 2016, now Pat. No. 9,974,518, which is a
(Continued)

(51) Int. Cl.
*H01L 41/047* (2006.01)
*H01L 41/09* (2006.01)
(Continued)

(52) U.S. Cl.
CPC ............. *A61B 8/4483* (2013.01); *A61B 8/12* (2013.01); *B06B 1/0662* (2013.01);
(Continued)

(58) Field of Classification Search
CPC ....... A61B 8/4483; A61B 8/12; B06B 1/0662; B06B 1/0688; H01L 41/047;
(Continued)

(56) References Cited

U.S. PATENT DOCUMENTS

| 5,176,140 A | 5/1993 | Kami et al. |
| 5,243,988 A | 9/1993 | Sieben et al. |

(Continued)

FOREIGN PATENT DOCUMENTS

| JP | H-08191835 A | 7/1996 |
| JP | 2005051689 A | 2/2005 |

(Continued)

OTHER PUBLICATIONS

International Searching Authority/European Patent Office, "Communication—Supplementary Search Report," for European Application No. 138 69083.9, dated Aug. 4, 2016, 12 pages.
(Continued)

*Primary Examiner* — Thomas Dougherty (57) ABSTRACT

The present disclosure provides a method of fabricating an ultrasound transducer. A substrate having a first side and a second side opposite the first side is provided. A bottom electrode is formed over the first side of the substrate. A piezoelectric element is formed over the bottom electrode. The piezoelectric element has a chamfered sidewall. A top electrode is formed over the piezoelectric element. A step metal element is formed over a portion of the top electrode proximate to the chamfered sidewall of the piezoelectric element.

13 Claims, 12 Drawing Sheets

Related U.S. Application Data continuation of application No. 14/106,897, filed on Dec. 16, 2013, now Pat. No. 9,312,470.

(60) Provisional application No. 61/747,498, filed on Dec. 31, 2012.

(51) Int. Cl.

| | | |
|---|---|---|
| *A61B 8/00* | (2006.01) | |
| *A61B 8/12* | (2006.01) | |
| *H01L 41/31* | (2013.01) | |
| *H01L 41/29* | (2013.01) | |
| *B06B 1/06* | (2006.01) | |
| *H01L 41/08* | (2006.01) | |
| *A61B 8/08* | (2006.01) | |

(52) U.S. Cl.
CPC .......... *B06B 1/0688* (2013.01); *H01L 41/047* (2013.01); *H01L 41/0472* (2013.01); *H01L 41/0477* (2013.01); *H01L 41/0825* (2013.01); *H01L 41/0973* (2013.01); *H01L 41/29* (2013.01); *H01L 41/31* (2013.01); *A61B 8/0891* (2013.01); *A61B 8/445* (2013.01); *A61B 8/4461* (2013.01); *H01L 41/098* (2013.01); *Y10T 29/42* (2015.01); *Y10T 29/49005* (2015.01); *Y10T 29/49126* (2015.01); *Y10T 29/49155* (2015.01)

(58) Field of Classification Search
CPC ............... H01L 41/0472; H01L 41/082; H01L 41/0973; H01L 41/29; H01L 41/31; Y10T 29/42; Y10T 29/49005; Y10T 29/49
USPC ........ 310/320, 322, 328, 365, 366, 367–370
See application file for complete search history.

(56) References Cited

U.S. PATENT DOCUMENTS

| | | | |
|---|---|---|---|
| 5,376,857 A | 12/1994 | Takeuchi et al. | |
| 5,488,954 A | 2/1996 | Sleva et al. | |
| 5,546,948 A | 8/1996 | Hamm et al. | |
| 6,443,900 B2 | 9/2002 | Adachi et al. | |
| 7,498,904 B2 | 3/2009 | Ohara et al. | |
| 9,312,470 B2 * | 4/2016 | Rice | B06B 1/0662 |
| 2002/0077551 A1 | 6/2002 | Fleischman et al. | |
| 2003/0003630 A1 | 2/2003 | Limura et al. | |
| 2004/0214371 A1 | 10/2004 | Mahmood | |
| 2006/0011701 A1 | 1/2006 | Duan et al. | |
| 2007/0057599 A1 | 3/2007 | Motai et al. | |
| 2007/0220723 A1 | 9/2007 | Furuya et al. | |
| 2008/0224569 A1 | 9/2008 | Ohashi et al. | |
| 2009/0229126 A1 | 9/2009 | Oguri | |
| 2009/0284102 A1 | 11/2009 | Karakaya et al. | |
| 2010/0160788 A1 | 6/2010 | Davies et al. | |
| 2010/0179430 A1 | 7/2010 | Sano et al. | |
| 2011/0024274 A1 | 2/2011 | Yoshihara et al. | |

FOREIGN PATENT DOCUMENTS

| | | |
|---|---|---|
| JP | 2005110116 A | 4/2005 |
| JP | 2006254295 A | 9/2006 |
| JP | 2012175507 A | 9/2012 |
| WO | 2012075129 A1 | 6/2012 |
| WO | 2012075153 A1 | 6/2012 |

OTHER PUBLICATIONS

International Search Report and Written Opinion received in corresponding Patent Cooperation Treaty Application No. PCT/US2013/077502 dated Apr. 23, 2014, 13 pages.

\* cited by examiner

ULTRASONIC TRANSDUCER ELECTRODE ASSEMBLY

PRIORITY DATA

This application is a Continuation of U.S. application Ser. No. 15/094,717, filed Apr. 8, 2016, which is a Continuation of U.S. patent application Ser. No. 14/106,897, filed Dec. 16, 2013, now U.S. Pat. No. 9,312,470, which claims priority to Provisional Patent Application No. 61/747,498, filed Dec. 31, 2012, the disclosures of which are hereby incorporated by reference in their entireties.

TECHNICAL FIELD

The present disclosure relates generally to intravascular ultrasound (IVUS) imaging, and in particular, to electrode assembly of an ultrasound transducer.

BACKGROUND

Intravascular ultrasound (IVUS) imaging is widely used in interventional cardiology as a diagnostic tool for assessing a vessel, such as an artery, within the human body to determine the need for treatment, to guide intervention, and/or to assess its effectiveness. An IVUS imaging system uses ultrasound echoes to form a cross-sectional image of the vessel of interest. Typically, IVUS imaging uses a transducer on an IVUS catheter that both emits ultrasound signals (waves) and receives the reflected ultrasound signals. The emitted ultrasound signals (often referred to as ultrasound pulses) pass easily through most tissues and blood, but they are partially reflected as the result of impedance variations arising from tissue structures (such as the various layers of the vessel wall), red blood cells, and other features of interest. The IVUS imaging system, which is connected to the IVUS catheter by way of a patient interface module, processes the received ultrasound signals (often referred to as ultrasound echoes) to produce a cross-sectional image of the vessel where the IVUS catheter is located.

IVUS catheters typically employ one or more transducers to transmit ultrasound signals and receive reflected ultrasound signals. These transducers have electrodes that are used to apply electrical signals to the transducers. However, existing techniques of forming electrodes for transducers may have certain shortcomings. For example, the electrodes of conventional transducers may suffer from discontinuity problems.

Therefore, while conventional methods of forming transducer electrodes are generally adequate for their intended purposes, they have not been entirely satisfactory in every aspect.

SUMMARY

Ultrasounds transducers are used in Intravascular ultrasound (IVUS) imaging to help assess medical conditions inside a human body. As a part of its operation, an ultrasound transducer has electrodes that are used to apply electrical signals to the transducer. However, conventional ultrasound transducers may suffer from drawbacks such as electrode discontinuity, which may interfere with the intended electrical operation of the transducer. The present disclosure is directed to an ultrasound transducer that utilizes a step metal element to overcome the electrode discontinuity issues associated with conventional ultrasound transducers. In more detail, the ultrasound transducer has a piezoelectric film that is sandwiched between a top electrode and a bottom electrode. The top electrode is located on a top surface and a sidewall of the piezoelectric film. The portion of the top electrode located on the sidewall of the piezoelectric film is prone to suffer from discontinuity problems. Therefore, a step metal element—having the same material composition as the top electrode itself—is formed on the sidewall portion of the top electrode. The step metal element serves as a bridge in case electrical discontinuity occurs in the sidewall portion of the top electrode.

The present disclosure provides various embodiments of an ultrasound transducer for use in intravascular ultrasound (IVUS) imaging. An exemplary ultrasound transducer includes a substrate; a bottom electrode disposed over the substrate; a piezoelectric element disposed over the bottom electrode; a top electrode disposed over at least a top surface and a sidewall of the piezoelectric element; and a step metal element disposed over a sidewall of the top electrode.

The present disclosure further provides an ultrasound system. The ultrasound system includes: an imaging component that includes a flexible elongate member and a piezoelectric micromachined ultrasound transducer (PMUT) coupled to a distal end of the elongate member. The PMUT includes: a substrate having a front surface and a back surface opposite the first surface; a well located in the substrate, the well extending from the back surface of the substrate to, but not beyond, the front surface of the substrate, wherein the well is at least partially filled with a backing material; a transducer membrane disposed over the well, wherein the transducer member includes a piezoelectric element disposed between a top electrode and a bottom electrode; and a step metal element disposed over a sidewall of the piezoelectric element. The ultrasound system also includes an interface module configured to engage with a proximal end of the elongate member; and an ultrasound processing component in communication with the interface module.

The present disclosure further provides a method of forming an ultrasound transducer. The method includes: providing a substrate having a first side and a second side opposite the first side; forming a bottom electrode over the first side of the substrate; forming a piezoelectric element over the bottom electrode, the piezoelectric element having a chamfered sidewall; forming a top electrode over the piezoelectric element; and forming a step metal element over a portion of the top electrode proximate to the chamfered sidewall of the piezoelectric element.

Both the foregoing general description and the following detailed description are exemplary and explanatory in nature and are intended to provide an understanding of the present disclosure without limiting the scope of the present disclosure. In that regard, additional aspects, features, and advantages of the present disclosure will become apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, the present disclosure provides an ultrasound imaging system described in terms of cardiovascular imaging, however, it is understood that such description is not intended to be limited to this application. In some embodiments, the ultrasound imaging system includes an intravascular imaging system. The imaging system is equally well suited to any application requiring imaging within a small cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

There are primarily two types of catheters in common use today: solid-state and rotational. An exemplary solid-state catheter uses an array of transducers (typically 64) distributed around a circumference of the catheter and connected to an electronic multiplexer circuit. The multiplexer circuit selects transducers from the array for transmitting ultrasound signals and receiving reflected ultrasound signals. By stepping through a sequence of transmit-receive transducer pairs, the solid-state catheter can synthesize the effect of a mechanically scanned transducer element, but without moving parts. Since there is no rotating mechanical element, the transducer array can be placed in direct contact with blood and vessel tissue with minimal risk of vessel trauma, and the solid-state scanner can be wired directly to the imaging system with a simple electrical cable and a standard detachable electrical connector.

An exemplary rotational catheter includes a single transducer located at a tip of a flexible driveshaft that spins inside a sheath inserted into the vessel of interest. The transducer is typically oriented such that the ultrasound signals propagate generally perpendicular to an axis of the catheter. In the typical rotational catheter, a fluid-filled (e.g., saline-filled) sheath protects the vessel tissue from the spinning transducer and driveshaft while permitting ultrasound signals to freely propagate from the transducer into the tissue and back. As the driveshaft rotates (for example, at 30 revolutions per second), the transducer is periodically excited with a high voltage pulse to emit a short burst of ultrasound. The ultrasound signals are emitted from the transducer, through the fluid-filled sheath and sheath wall, in a direction generally perpendicular to an axis of rotation of the driveshaft. The same transducer then listens for returning ultrasound signals reflected from various tissue structures, and the imaging system assembles a two dimensional image of the vessel cross-section from a sequence of several hundred of these ultrasound pulse/echo acquisition sequences occurring during a single revolution of the transducer.

Figure 1:
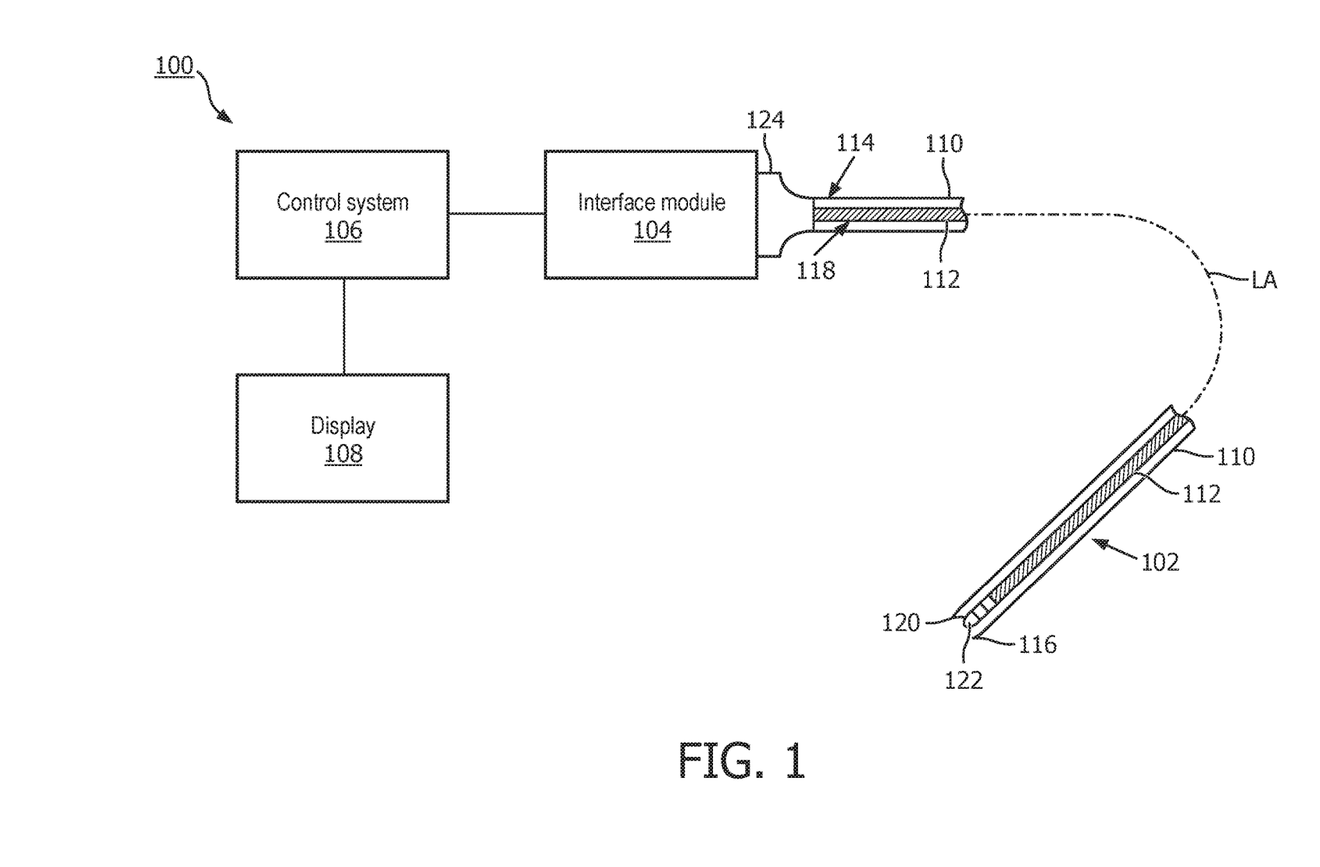
FIG. 1 is a schematic illustration of an intravascular ultrasound (IVUS) imaging system according to various aspects of the present disclosure.

FIG. 1 is a schematic illustration of an ultrasound imaging system 100 according to various aspects of the present disclosure. In some embodiments, the ultrasound imaging system 100 includes an intravascular ultrasound imaging system (IVUS). The IVUS imaging system 100 includes an IVUS catheter 102 coupled by a patient interface module (PIM) 104 to an IVUS control system 106. The control system 106 is coupled to a monitor 108 that displays an IVUS image (such as an image generated by the IVUS system 100).

In some embodiments, the IVUS catheter 102 is a rotational IVUS catheter, which may be similar to a Revolution® Rotational IVUS Imaging Catheter available from Volcano Corporation and/or rotational IVUS catheters disclosed in U.S. Pat. No. 5,243,988 and U.S. Pat. No. 5,546,948, both of which are incorporated herein by reference in their entirety. The catheter 102 includes an elongated, flexible catheter sheath 110 (having a proximal end portion 114 and a distal end portion 116) shaped and configured for insertion into a lumen of a blood vessel (not shown). A longitudinal axis LA of the catheter 102 extends between the proximal end portion 114 and the distal end portion 116. The catheter 102 is flexible such that it can adapt to the curvature of the blood vessel during use. In that regard, the curved configuration illustrated in FIG. 1 is for exemplary purposes and in no way limits the manner in which the catheter 102 may curve in other embodiments. Generally, the catheter 102 may be configured to take on any desired straight or arcuate profile when in use.

A rotating imaging core 112 extends within the sheath 110. The imaging core 112 has a proximal end portion 118 disposed within the proximal end portion 114 of the sheath 110 and a distal end portion 120 disposed within the distal end portion 116 of the sheath 110. The distal end portion 116 of the sheath 110 and the distal end portion 120 of the imaging core 112 are inserted into the vessel of interest during operation of the IVUS imaging system 100. The usable length of the catheter 102 (for example, the portion that can be inserted into a patient, specifically the vessel of interest) can be any suitable length and can be varied depending upon the application. The proximal end portion 114 of the sheath 110 and the proximal end portion 118 of the imaging core 112 are connected to the interface module 104. The proximal end portions 114, 118 are fitted with a catheter hub 124 that is removably connected to the interface module 104. The catheter hub 124 facilitates and supports a rotational interface that provides electrical and mechanical coupling between the catheter 102 and the interface module 104.

The distal end portion 120 of the imaging core 112 includes a transducer assembly 122. The transducer assembly 122 is configured to be rotated (either by use of a motor or other rotary devices or methods) to obtain images of the vessel. The transducer assembly 122 can be of any suitable type for visualizing a vessel and, in particular, a stenosis in a vessel. In the depicted embodiment, the transducer assembly 122 includes a piezoelectric micromachined ultrasonic transducer ("PMUT") transducer and associated circuitry, such as an application-specific integrated circuit (ASIC). An exemplary PMUT used in IVUS catheters may include a polymer piezoelectric membrane, such as that disclosed in U.S. Pat. No. 6,641,540, hereby incorporated by reference in its entirety. The PMUT transducer can provide greater than 75% bandwidth for optimum resolution in a radial direction, and a spherically-focused aperture for optimum azimuthal and elevation resolution.

The transducer assembly 122 may also include a housing having the PMUT transducer and associated circuitry disposed therein, where the housing has an opening that ultrasound signals generated by the PMUT transducer travel through. Alternatively, the transducer assembly 122 includes a capacitive micromachined ultrasonic transducer ("CMUT"). In yet another alternative embodiment, the transducer assembly 122 includes an ultrasound transducer array (for example, arrays having 16, 32, 64, or 128 elements are utilized in some embodiments).

The rotation of the imaging core 112 within the sheath 110 is controlled by the interface module 104, which provides user interface controls that can be manipulated by a user. The interface module 104 can receive, analyze, and/or display information received through the imaging core 112. It will be appreciated that any suitable functionality, controls, information processing and analysis, and display can be incorporated into the interface module 104. In an example, the interface module 104 receives data corresponding to ultrasound signals (echoes) detected by the imaging core 112 and forwards the received echo data to the control system 106. In an example, the interface module 104 performs preliminary processing of the echo data prior to transmitting the echo data to the control system 106. The interface module 104 may perform amplification, filtering, and/or aggregating of the echo data. The interface module 104 can also supply high- and low-voltage DC power to support operation of the catheter 102 including the circuitry within the transducer assembly 122.

In some embodiments, wires associated with the IVUS imaging system 100 extend from the control system 106 to the interface module 104 such that signals from the control system 106 can be communicated to the interface module 104 and/or vice versa. In some embodiments, the control system 106 communicates wirelessly with the interface module 104. Similarly, it is understood that, in some embodiments, wires associated with the IVUS imaging system 100 extend from the control system 106 to the monitor 108 such that signals from the control system 106 can be communicated to the monitor 108 and/or vice versa. In some embodiments, the control system 106 communicates wirelessly with the monitor 108.

FIGS. 2-14 are diagrammatic fragmentary cross-sectional side views of an example ultrasound transducer 200 to illustrate an electrode assembly for the transducer 200. The FIGS. 2-14 correspond to different stages of fabrication in accordance with various aspects of the present disclosure. FIGS. 2-14 have been simplified for the sake of clarity to better understand the inventive concepts of the present disclosure.

The ultrasound transducers 200 can each be included in the IVUS imaging system 100 of FIG. 1, for example in the transducer assembly 122. The ultrasonic transducer 200 has a small size and achieves a high resolution, so that it is well suited for intravascular imaging. In some embodiments, the ultrasonic transducer 200 has a size on the order of tens or hundreds of microns, can operate in a frequency range between about 1 mega-Hertz (MHz) to about 135 MHz, and can provide sub 50 micron resolution while providing depth penetration of at least 10 millimeters (mm). Furthermore, the ultrasonic transducer 200 is also shaped in a manner to allow a developer to define a target focus area based on a deflection depth of a transducer aperture, thereby generating an image that is useful for defining vessel morphology, beyond the surface characteristics. The various aspects of the ultrasound transducer 200 and its fabrication are discussed in greater detail below.

In the depicted embodiment, the ultrasound transducer 200 is a piezoelectric micromachined ultrasound transducer (PMUT). In other embodiments, the transducer 200 may include an alternative type of transducer. Additional features can be added in the ultrasound transducer 200, and some of the features described below can be replaced or eliminated for additional embodiments of the ultrasound transducer 200.

Figure 2:
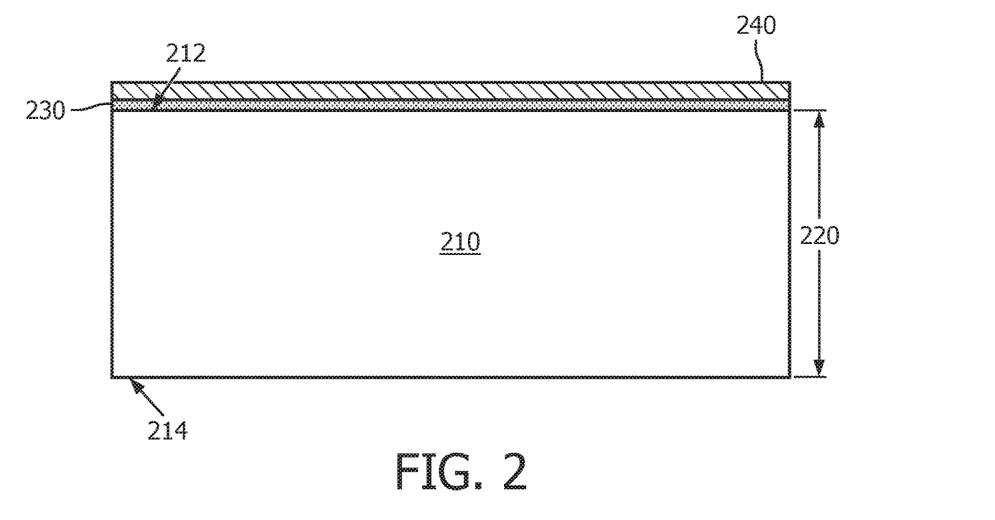
FIGS. 2-14 are diagrammatic cross-sectional side views of an ultrasound transducer at different stages of fabrication according to various aspects of the present disclosure.

As is shown in FIG. 2, the transducer 200 includes a substrate 210. The substrate 210 has a surface 212 and a surface 214 that is opposite the surface 212. The surface 212 may also be referred to as a front surface or a front side, and the surface 214 may also be referred to as a back surface or a back side. In the depicted embodiment, the substrate 210 is a silicon microelectromechanical system (MEMS) substrate. The substrate 210 includes another suitable material depending on design requirements of the PMUT transducer 200 in alternative embodiments. In the illustrated embodiments, the substrate 210 is a "lightly-doped silicon substrate." In other words, the substrate 210 comes from a silicon wafer that is lightly doped with a dopant and as a result has a resistivity in a range from about 1 ohms/cm to about 1000 ohms/cm. One benefit of the "lightly-doped silicon substrate" 210 is that it is relatively inexpensive, for example in comparison with pure silicon or undoped silicon substrates. Of course, it is understood that in alternative embodiments where cost is not as important of a concern, pure silicon or undoped silicon substrates may also be used.

The substrate 210 may also include various layers that are not separately depicted and that can combine to form electronic circuitry, which may include various microelectronic elements. These microelectronic elements may include: transistors (for example, metal oxide semiconductor field effect transistors (MOSFET), complementary metal oxide semiconductor (CMOS) transistors, bipolar junction transistors (BJT), high voltage transistors, high frequency transistors, p-channel and/or n-channel field effect transistors (PFETs/NFETs)); resistors; diodes; capacitors; inductors; fuses; and/or other suitable elements. The various layers may include high-k dielectric layers, gate layers, hard mask layers, interfacial layers, capping layers, diffusion/barrier layers, dielectric layers, conductive layers, other suitable layers, or combinations thereof. The microelectronic elements could be interconnected to one another to form a portion of an integrated circuit, such as a logic device, memory device (for example, a static random access memory (SRAM)), radio frequency (RF) device, input/output (I/O) device, system-on-chip (SoC) device, other suitable types of devices, or combinations thereof.

An initial thickness 220 of the substrate 210 is measured between the surface 212 and the surface 214. In some embodiments, an initial thickness 220 is in a range from about 200 microns (um) to about 1000 um.

A dielectric layer 230 is formed over the surface 212 and 214 of the substrate 210. The dielectric layer 230 may be formed by a suitable deposition process known in the art, such as thermal oxidation, low temperature oxide deposition, chemical vapor deposition (CVD), physical vapor deposition (PVD), atomic layer deposition (ALD), or combinations thereof. The dielectric layer 230 may contain an oxide material or a nitride material, for example silicon oxide, phosphosilicate glass (PSG), silicon nitride, silicon oxynitride or combination thereof. The dielectric layer 230 provides a support surface for the layers to be formed thereon. The dielectric layer 230 also provides electrical insulation. In more detail, the substrate 210 in the illustrated embodiments is a "lightly-doped silicon substrate" that is relatively conductive, as discussed above. This relatively high conductivity of the substrate 210 may pose a problem when the transducer 200 is pulsed with a relatively high voltage, for example with an excitation voltage of about 60 volts to about 200 volts DC. This means that it is undesirable for a bottom electrode (discussed below in more detail) of the transducer 200 to come into direct contact with the silicon substrate 210. According to the various aspects of the present disclosure, the dielectric layer 230 helps insulate the bottom electrode of the transducer 230 from the relatively conductive surface of the silicon substrate 210.

A conductive layer 240 (i.e., the bottom electrode) is then formed over the dielectric layer 230. The conductive layer 240 may be formed by a suitable deposition process such as sputtering, evaporation, CVD, PVD, ALD, etc. In the illustrated embodiment, the conductive layer 240 includes a metal or multiple metals material. For example, the metal or multiple metals material may include Titanium, Chromium, Gold, Aluminum, Platinum or combinations thereof.

Figure 3:
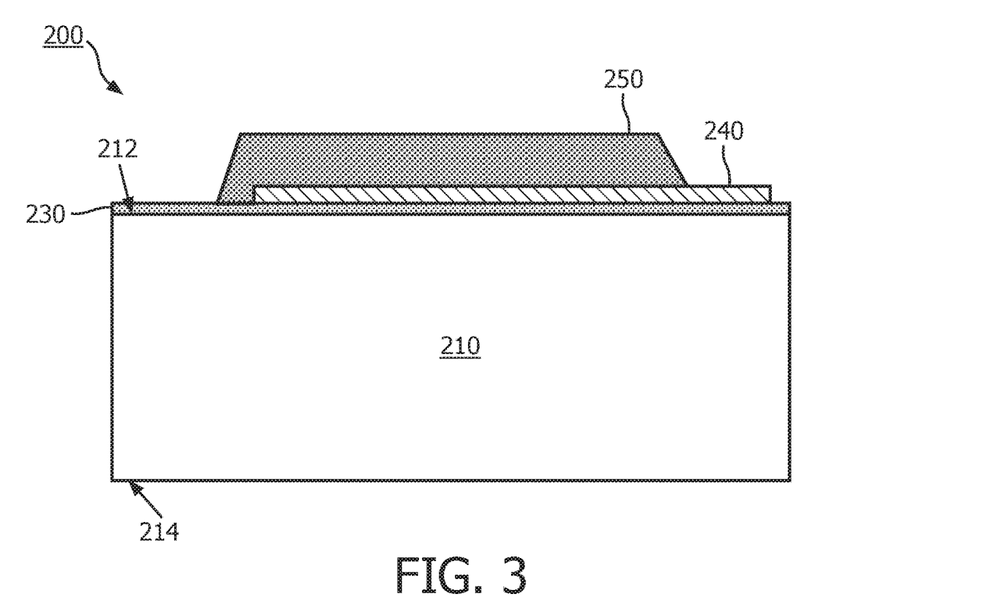

Referring now to FIG. 3, the conductive layer 240 is patterned using techniques in a lift-off or photolithography process. Unwanted portions of the conductive layer 240 are removed as a part of the process. In some embodiments, the conductive layer can be deposited with a shadow mask to create a pattern.

A piezoelectric film 250 is then formed over the dielectric layer 230 and the conductive layer 240. In various embodiments, the piezoelectric film 250 may include piezoelectric materials such as polyvinylidene fluoride (PVDF) or its co-polymers, polyvinylidene fluoride-trifluoroethylene (PVDF-TrFE), or polyvinylidene fluoride-tetrafluoroethylene (PVDF-TFE). Alternatively, polymers such as PVDF-CTFE and PVDF-CFE or sol-gel formed piezoelectric material may be used. In the illustrated embodiment, the piezoelectric material used in the piezoelectric film 250 contains PVDF-TrFE.

The piezoelectric film 250 is patterned to achieve a desired shape, for example the shapes shown in FIG. 3. Unwanted portions of the piezoelectric film 250 are removed in the patterning process. As a result, portions of the dielectric layer 230 and the conductive layer 240 are exposed. For reasons of simplicity, FIG. 3 only illustrates the piezoelectric film 250 after it has been patterned.

In the present embodiment, the piezoelectric film 250 is etched in a manner to form a chamfer to allow deposition for a top electrode to be formed. The chamfer may manifest itself as the trapezoidal sidewall shown in the cross-sectional view of FIG. 3. The chamfer allows a conductive layer 270 to be deposited over the piezoelectric film 250 with a lower likelihood of discontinuity. It is also understood that an adhesion-promoting layer (not illustrated herein) may be formed between the piezoelectric film 250 and the conductive layer 240 in some embodiments, so that the piezoelectric film 250 is more likely to stick to the conductive layer 240. One embodiment of the adhesion-promoting layer is discussed in detail in U.S. Provisional Application 61/745,212, titled "Methods and Apparatus for Focusing Miniature Ultrasound Transducers" to Dylan Van Hoven, filed on Dec. 21, 2012, attorney docket 44755.1061, the contents of which are incorporated by reference herein in its entirety.

Figure 4:
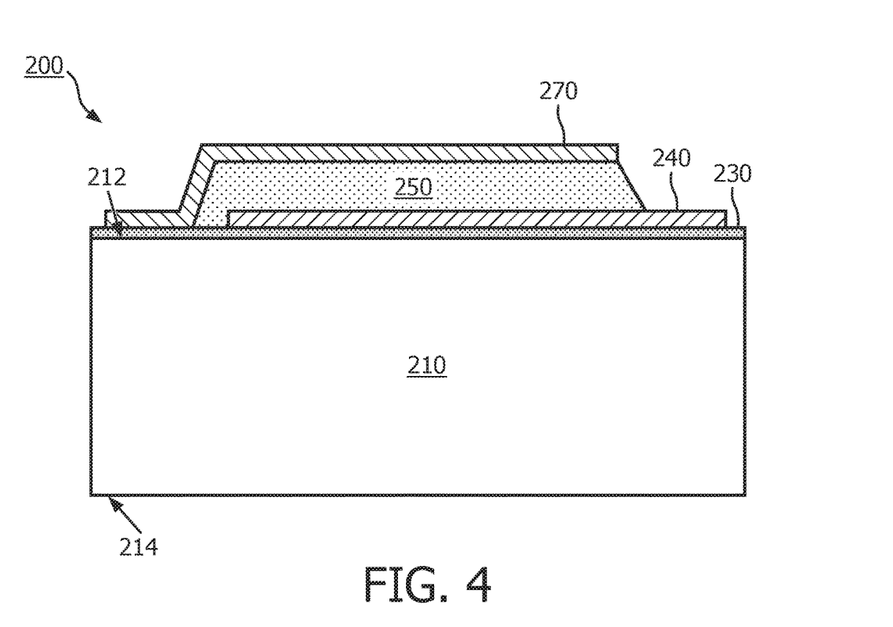
Figure 5:
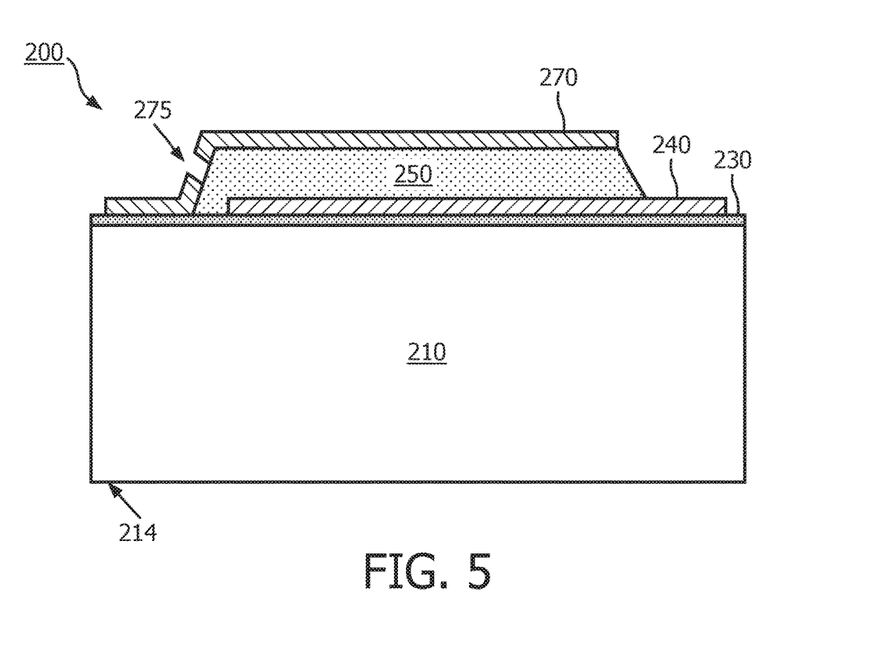

Referring now to FIG. 4, a conductive layer 270 (i.e., the top electrode) is formed over the piezoelectric film 250 using a suitable deposition process known in the art. In the illustrated embodiment, the conductive layer 270 includes a metal or multiple metals material, such as Titanium, Chromium, Gold, Aluminum, Platinum or combinations thereof. After its deposition, the conductive layer 270 is patterned using techniques in a photolithography process. Unwanted portions of the conductive layer 270 are removed as a part of the photolithography process. For reasons of simplicity, FIG. 4 only illustrates the conductive layer 270 after it has been patterned.

The conductive layers 240 and 270 and the piezoelectric layer 250 (and the adhesion-promoting layer in embodiments where it is used) may collectively be considered a transducer membrane. It is understood that pad metals may also be formed to establish electrical connections on the conductive layers 240 and/or 270, but these pad metals are not illustrated herein for reasons of simplicity.

A potential problem associated with the deposition of the conductive layer 270 (i.e., top electrode) is that there may be a discontinuity in the deposited conductive layer 270. For example, referring now to FIG. 5, an example discontinuity 275 in the conductive layer 270 is shown. As discussed above, the piezoelectric film 250 is formed to have a chamfer partly to avoid such discontinuity 275. Nevertheless, limitations in the metal deposition process and other imperfections may still lead to one or more discontinuities 275. The discontinuity 275 may cause an electrical open condition. In other words, the conductive layer 270 may not be electrically connected to intended external devices due to the discontinuity 275. This may prevent full electrical access to the transducer 200.

According to various aspects of the present disclosure, the problems caused by the discontinuity 275 may be resolved using a step metal element. Step metal can be formed by a suitable deposition process such as sputtering, evaporation, CVD, PVD, ALD, etc., followed by lift-off or photolithography pattern process. The formation of the step metal is discussed below with reference to FIGS. 6-9.

Figure 6:
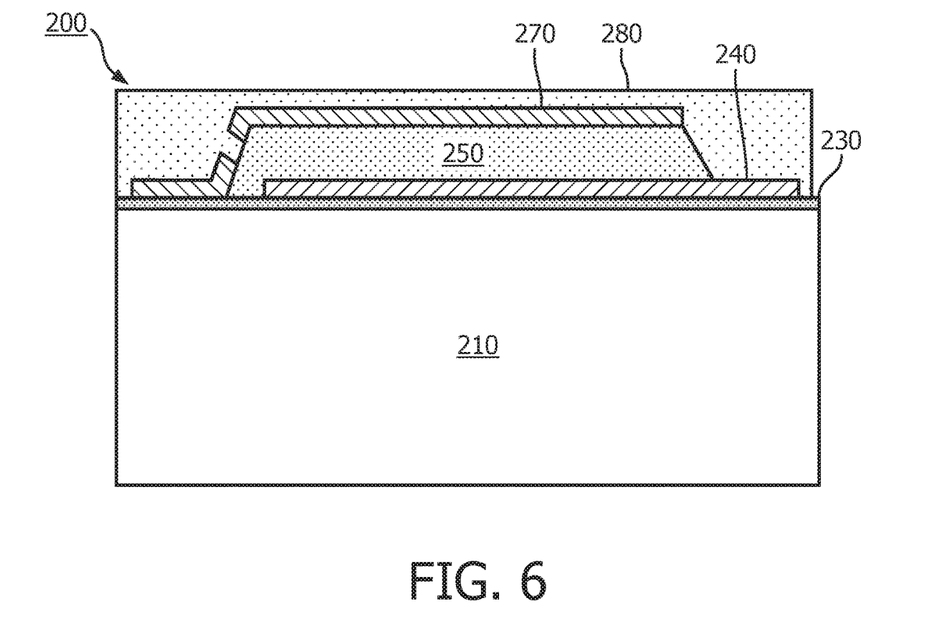

Referring to FIG. 6, a photoresist material 280 is coated over the transducer 200, including over the conductive layer 270.

Figure 7:
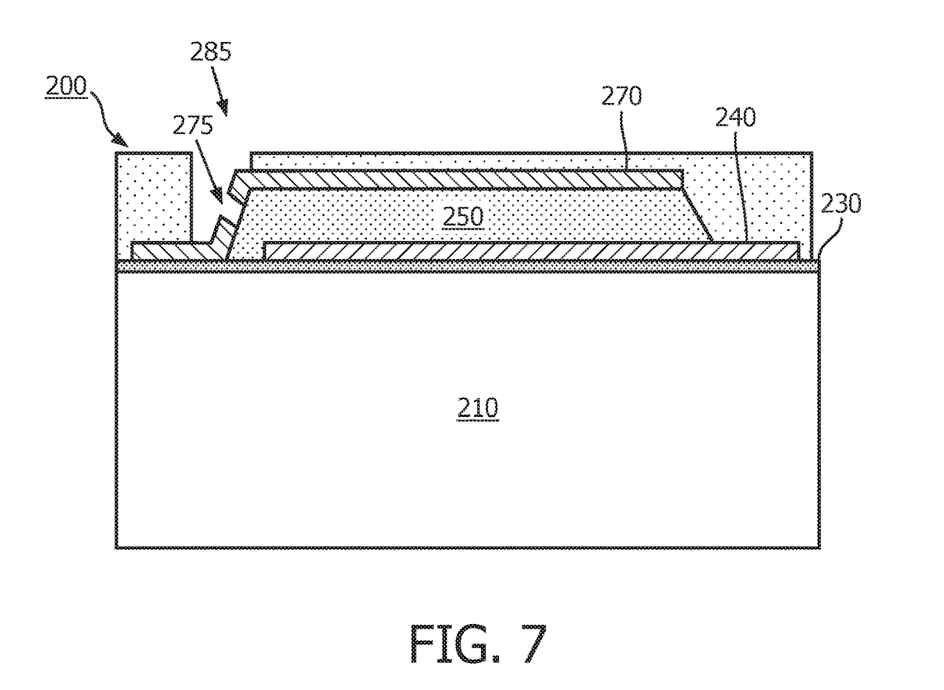

Referring now to FIG. 7, an opening 285 is formed in the photoresist material 280. The opening 285 is configured to be wide enough to expose a sidewall portion of the conductive layer 270 (i.e., the portion of the top electrode formed on the sidewall of the piezoelectric film 250). If the discontinuity 275 exists, the opening 285 exposes the discontinuity 275 as well.

Figure 8:
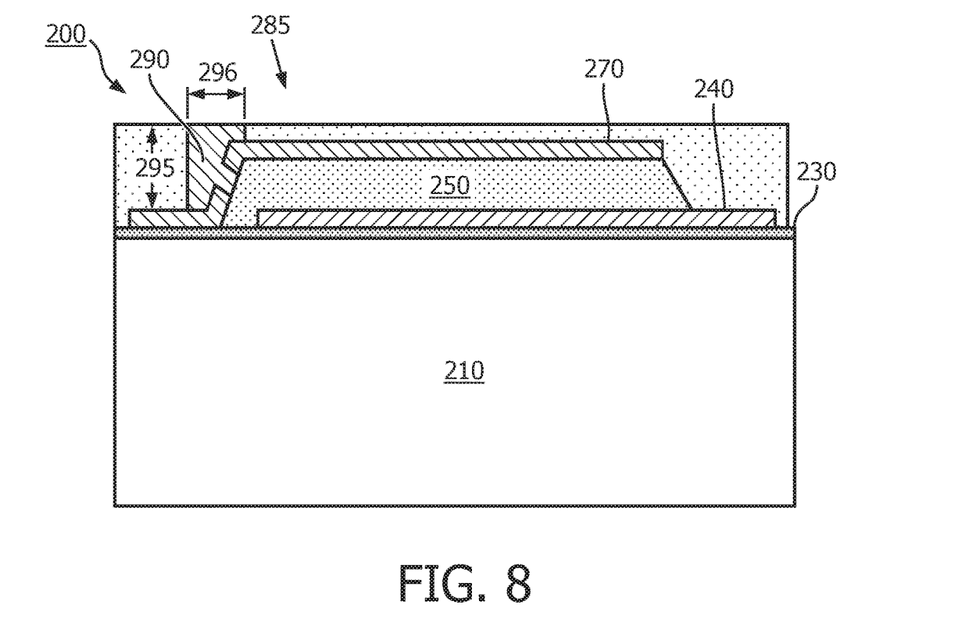

Referring now to FIG. 8, a step metal element 290 is formed in the opening 285. The step metal element 290 has a substantially similar material composition as the conductive layer 270. In other words, in the illustrated embodiment, the step metal element 290 includes one or more metals such as Titanium, Chromium, Gold, Aluminum, or combinations thereof. The step metal element 290 is formed to have a vertical dimension 295 and a lateral or horizontal dimension 296. In some embodiments, the vertical dimension 295 is in a range from about 0.5 um to about 2 um, and the lateral dimension 296 is in a range from about 30 um to about 100 um.

Figure 9:
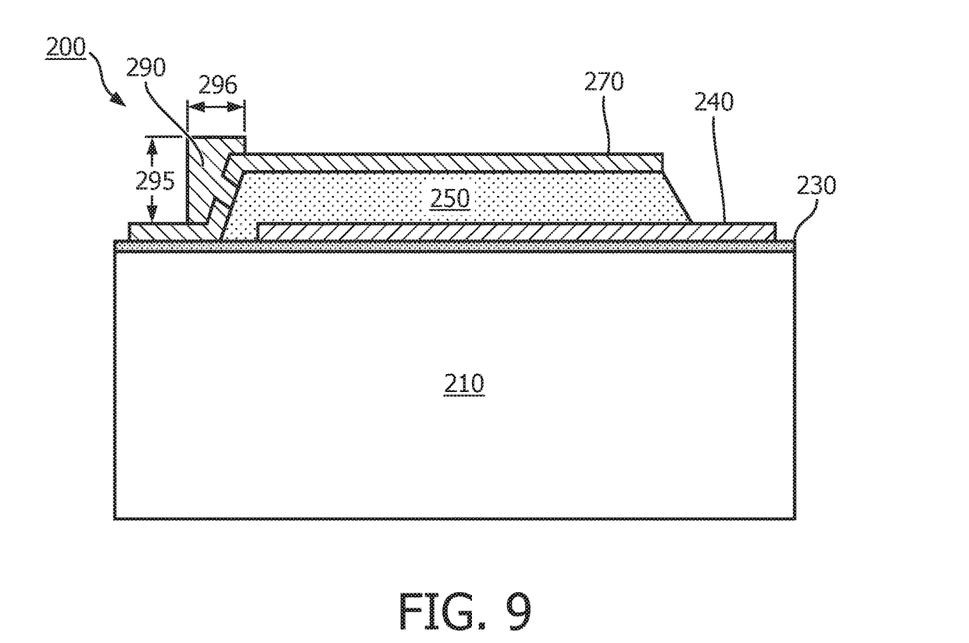

Referring now to FIG. 9, the photoresist material 280 is removed, for example through a photoresist stripping process. The step metal element 290 covers over the sidewall of the conductive layer 270 (top electrode). It can be seen that if any discontinuities such as the discontinuity 275 exist in the conductive layer 270, the step metal 290 would "cover up" the discontinuities. Stated differently, the step metal 290 in effect serves as a bridge for segments of the conductive layer 270 separated by the discontinuities. Consequently, electrical continuity is maintained throughout the conductive layer 270 due to the step metal 290.

It is understood that the step metal element 290 is formed on the sidewall of the conductive layer 270 because the sidewall of the conductive layer 270 has been identified as a segment of the conductive layer 270 where discontinuities are likely to occur. However, in alternative embodiments, the step metal element 290 (or other elements similar thereto) may be configured to form over other regions of the conductive layer 270, if those regions are also identified as likely to include discontinuities.

In addition to (or instead of) the step metal element 290, the present disclosure may also form a metal via to address the discontinuity issue discussed above, as discussed below in more detail with reference to FIGS. 10-14. For reasons of consistency and clarity, the same or similar components appearing in FIGS. 2-9 and 10-14 are labeled the same.

Figure 10:
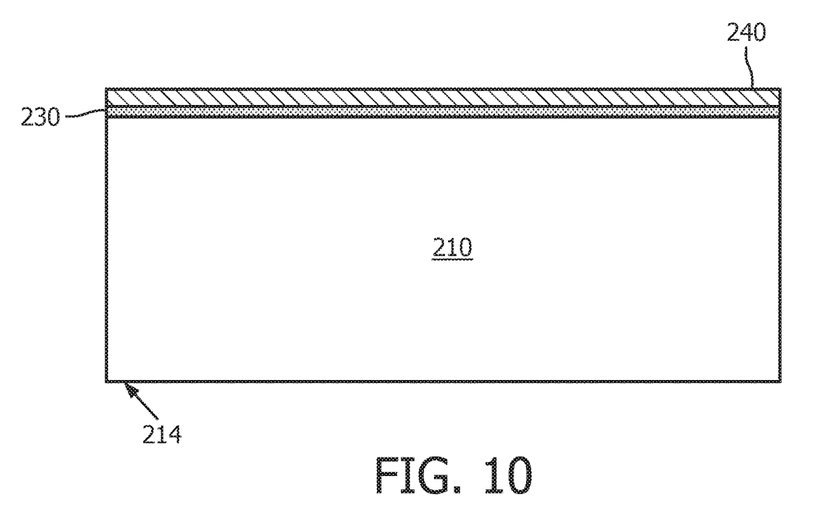

Referring now to FIG. 10, the dielectric layer 230 (discussed above with reference to FIG. 2) is formed over the substrate 210. The conductive layer 240 (discussed above with reference to FIG. 2) is then formed over the dielectric layer 230.

Figure 11:
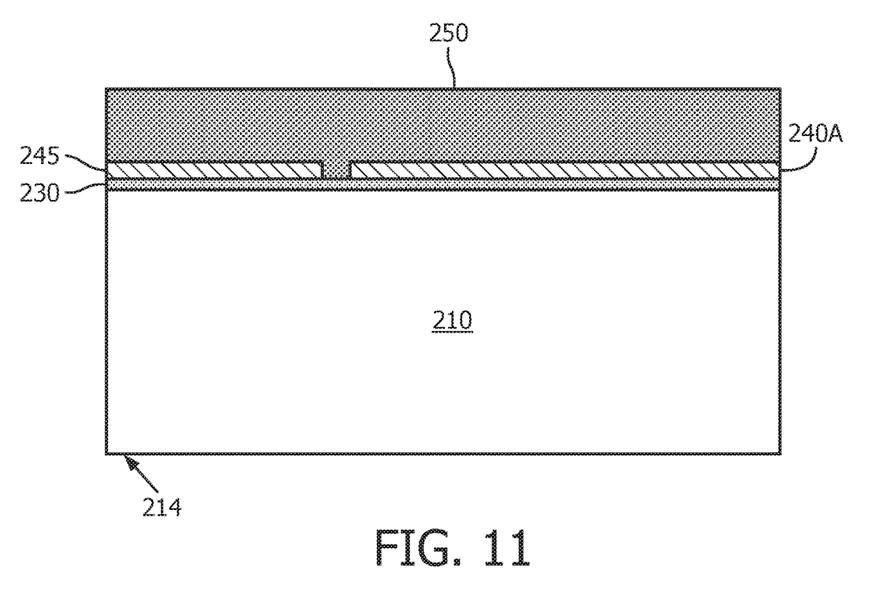

Referring now to FIG. 11, the conductive layer 240 is patterned into separate segments: a segment 240 and a segment 245. The segment 240 serves as the bottom electrode of the transducer 200 and will hereinafter be referred to as the bottom electrode 240A. The segment 245 serves as a bottom portion of the top electrode of the transducer 200 and will hereinafter be referred to as the top electrode segment 245. The piezoelectric film 250 is then formed over a portion of the bottom electrode 240A and over a portion of the top electrode segment 245. As discussed above, the piezoelectric film 250 may contain a PVDF material or another suitable polymer material.

Figure 12:
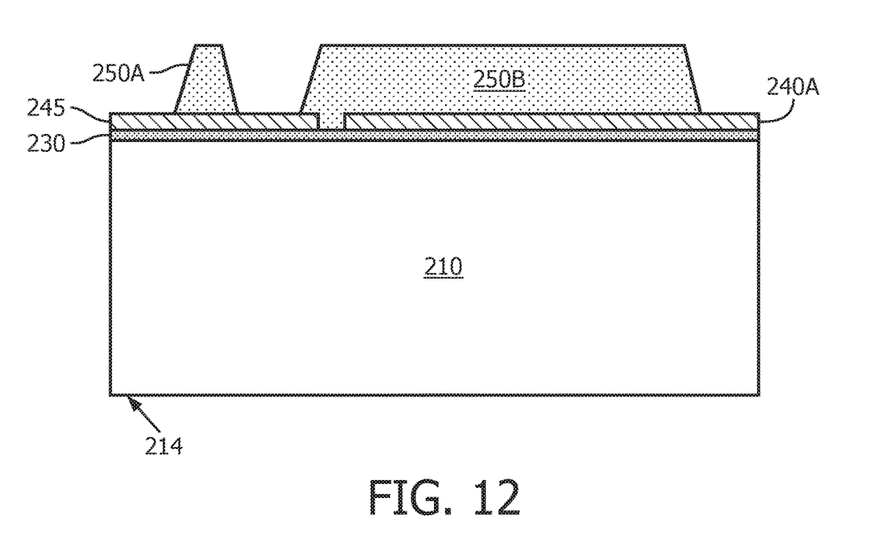

Referring now to FIG. 12, the piezoelectric film 250 is patterned with a via through to the segment 245. The via separates the piezoelectric film into two separate components 250A and 250B in this cross-sectional view. In some embodiments, the component 250A is formed over the top electrode segment 245, and the component 250B is formed over the bottom electrode 240A. However, this may not necessarily be the case in different embodiments. As discussed above, to alleviate electrode discontinuity concerns, both the components 250A and 250B are formed to have a chamfer.

Figure 13:
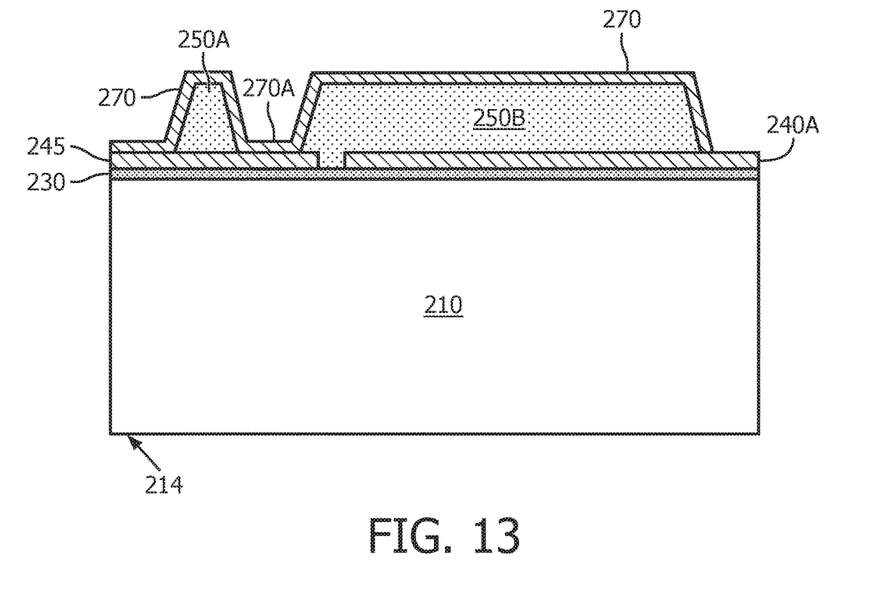

Referring now to FIG. 13, a conductive layer 270 is formed over the piezoelectric components 250A and 250B. The conductive layer 270 contains metal or multiple metals material, such as Titanium, Chromium, Gold, Aluminum, Platinum or combinations thereof. The conductive layer 270 serves as the top portion of the top electrode of the transducer 200 and will hereinafter be referred to as the top electrode segment 270.

As is shown in FIG. 13, a portion 270A of the top electrode segment 270 is formed on the top electrode segment 245. This portion 270A may be referred to as a via 270A. The via 270A in effect increases the contact surface between the top electrode segment 270 (i.e., the top part of the top electrode) and the top electrode segment 245 (i.e., the bottom part of the top electrode). As a result, discontinuity is less likely to appear in the top electrode.

Figure 14:
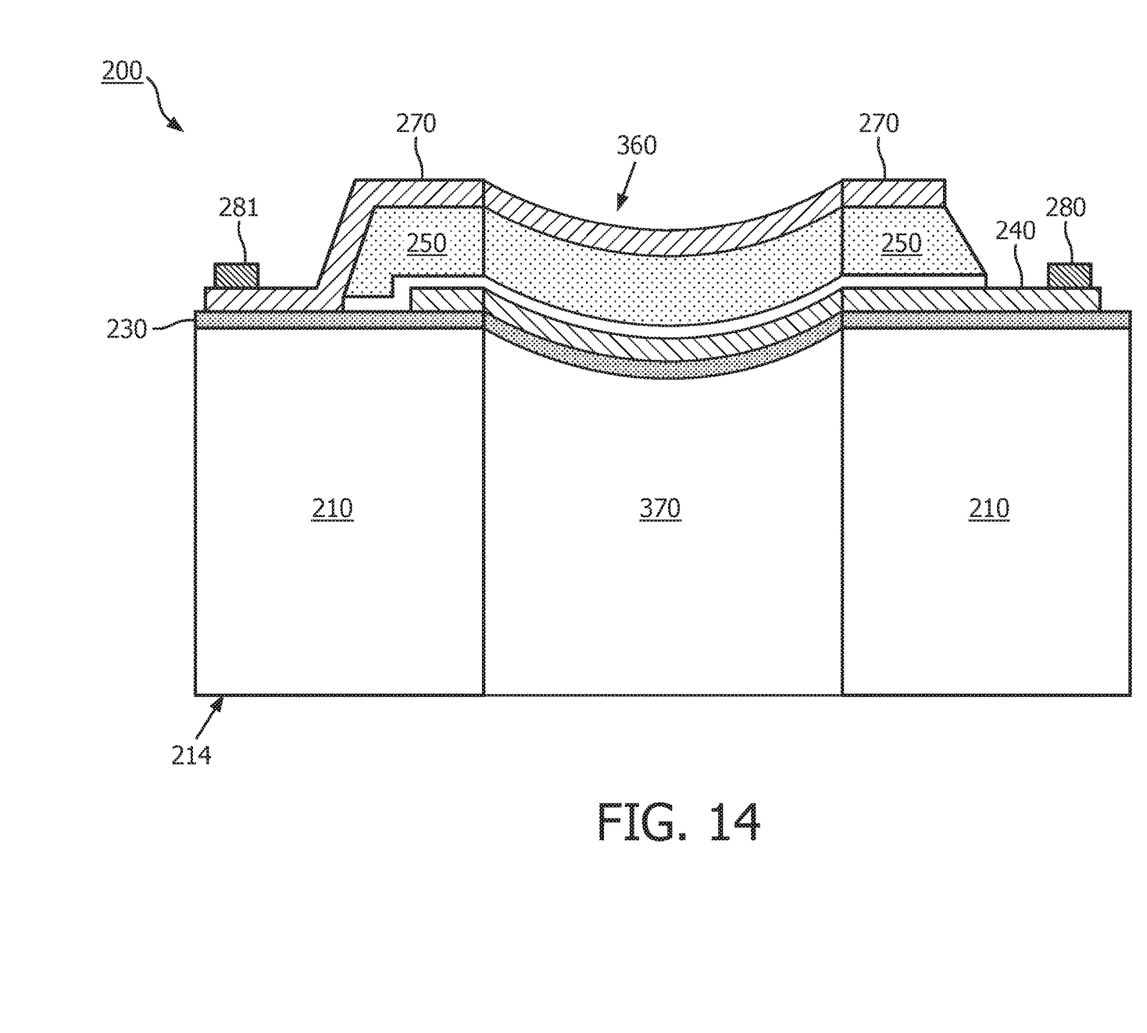

Additional processing steps may be performed to complete the fabrication of the transducer 200. For example, an opening or well may be etched into the substrate 210 from the back side 214. The opening or well may be filled with a backing material such as epoxy. The transducer membrane may also be deflected (for example by application of air pressure) into an arcuate shape such as illustrated in FIG. 14. These additional process steps are discussed in more detail in U.S. Provisional Application 61/745,212, titled "Methods and Apparatus for Focusing Miniature Ultrasound Transducers" to Dylan Van Hoven, filed on Dec. 21, 2012, attorney docket 44755.1061, the content of which is incorporated by reference herein in its entirety.

Figure 15:
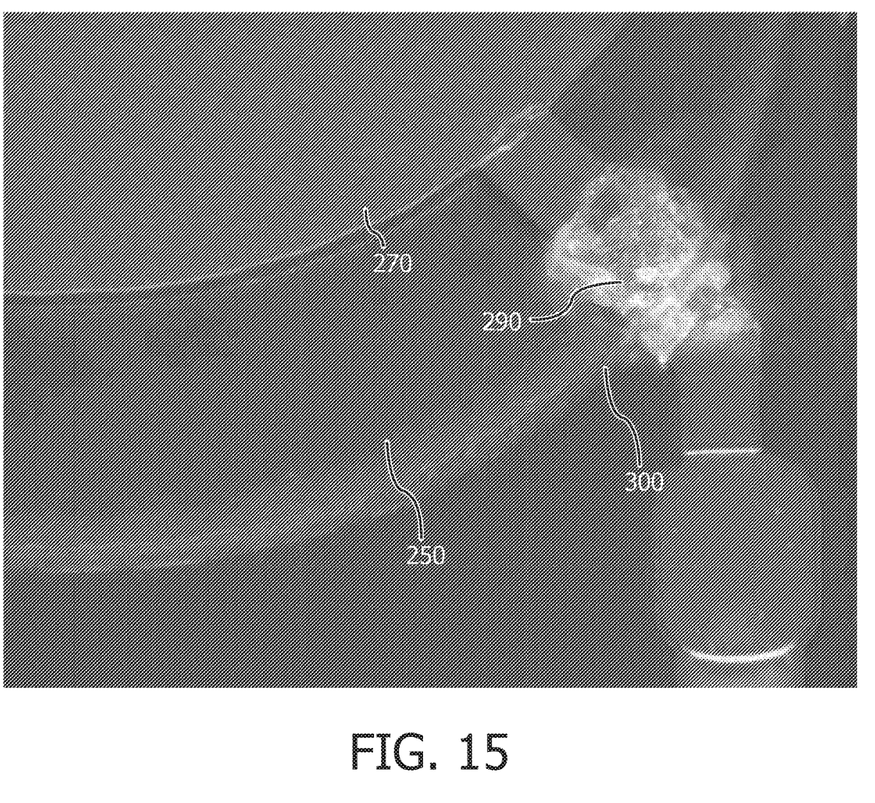
FIG. 15 is a diagrammatic top view of a portion of a transducer according to various aspects of the present disclosure.

FIG. 15 is a simplified diagrammatic top view of a portion of the transducer 200 that illustrates an embodiment of the step metal element 290 discussed above with reference to FIGS. 8-9. For reasons of consistency and clarity, similar components are labeled the same in FIGS. 8-9 and 15. As discussed above, the piezoelectric film 250 is formed to have a chamfer, which is labeled with the reference numeral 300 herein to allow for better electrode continuity. A segment of the top electrode 270 spans over the chamfer 300. The step metal element 290 is formed on the chamfer 300 to ensure electrical continuity of the top electrode 270.

Figure 16A:
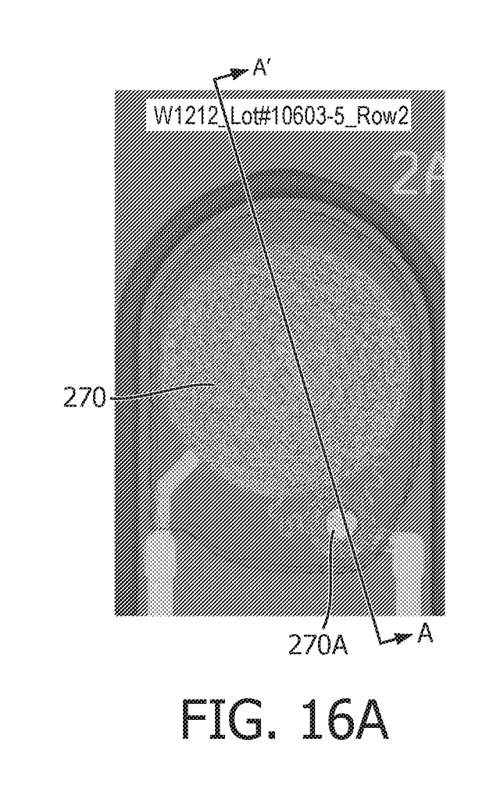
FIG. 16A, FIG. 16B, FIG. 16C, FIG. 16D, and FIG. 16E are diagrammatic top views of various vias according to various aspects of the present disclosure.

FIG. 16A is a simplified diagrammatic top view of a portion of the transducer 200 that illustrates an embodiment of the via 270A discussed above with reference to FIG. 13. For reasons of consistency and clarity, similar components are labeled the same in FIGS. 13 and 16A. The cross-sectional view of FIG. 13 is obtained by taking a cross-section from point A to A' in the top view of FIG. 16A. As is shown, the via 270A effectively increases a contact surface area between a top segment of the top electrode 270 and a bottom segment of the top electrode (not visible in FIG. 16A), thereby reducing risks of discontinuity.

It is also understood that in some embodiments, both the step metal element 290 and the via 270A may be implemented in a transducer 200 to further improve electrode continuity.

Figure 16B:
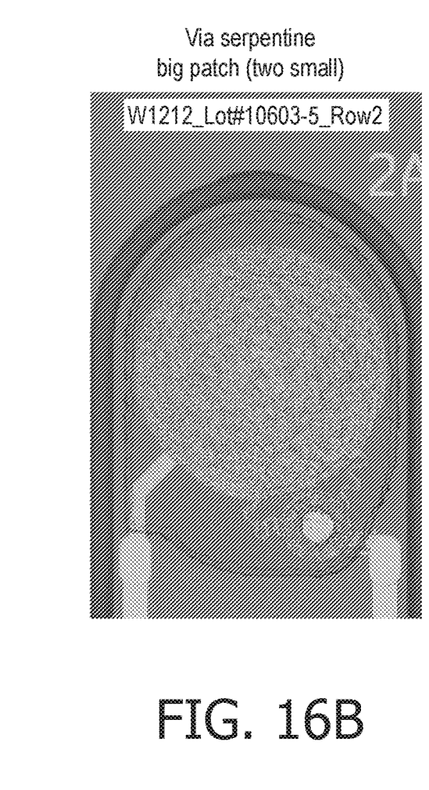
Figure 16C:
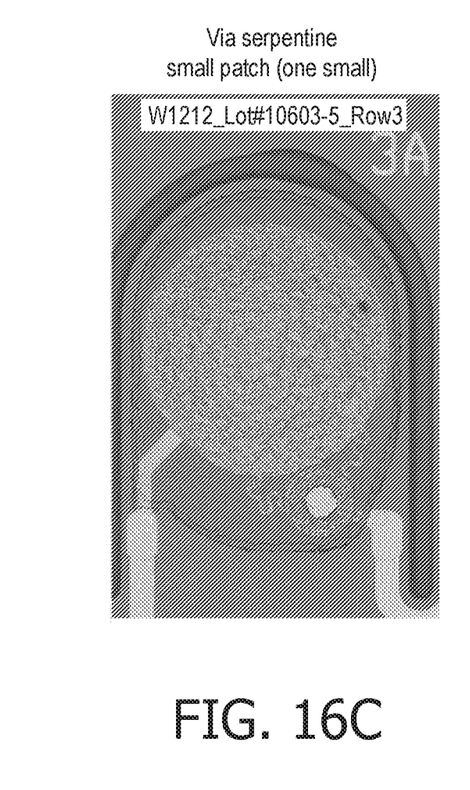
Figure 16D:
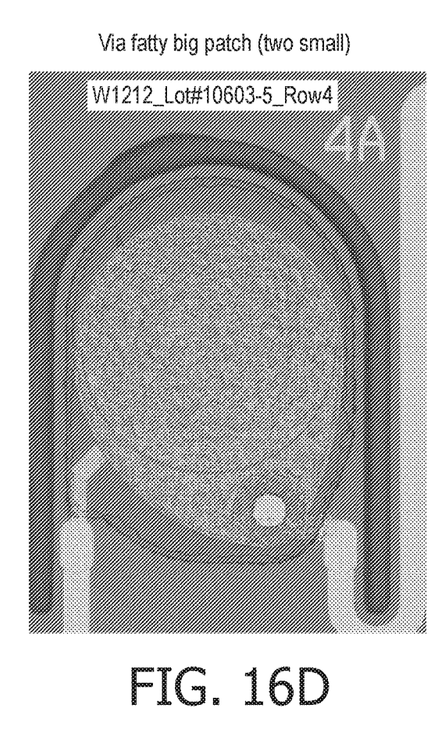
Figure 16E:
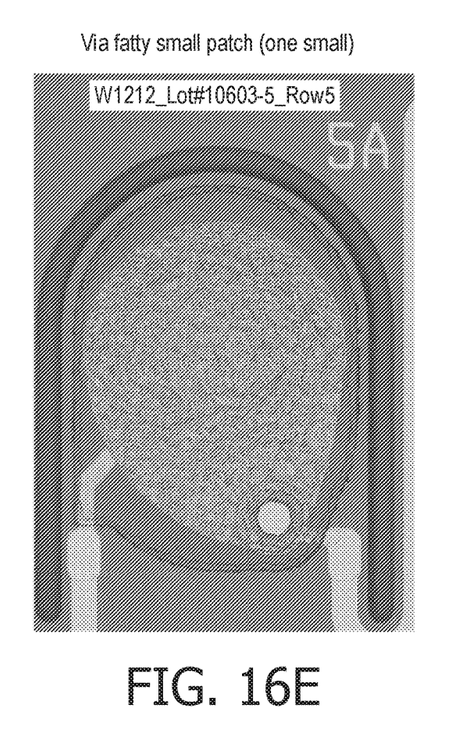

FIGS. 16B-16E illustrate diagrammatic top views of alternative embodiments of the via discussed above. For example, the embodiment shown in FIG. 16B illustrates a via serpentine big patch. The embodiment shown in FIG. 16C illustrates a via serpentine small patch. The embodiment shown in FIG. 16D illustrates a via fatty big patch. The embodiment shown in FIG. 16E illustrates a via fatty small patch. Regardless of the embodiment, however, it is understood that the big enhances the contact surface area for the top electrode and alleviates electrode discontinuity concerns.

Figure 17:
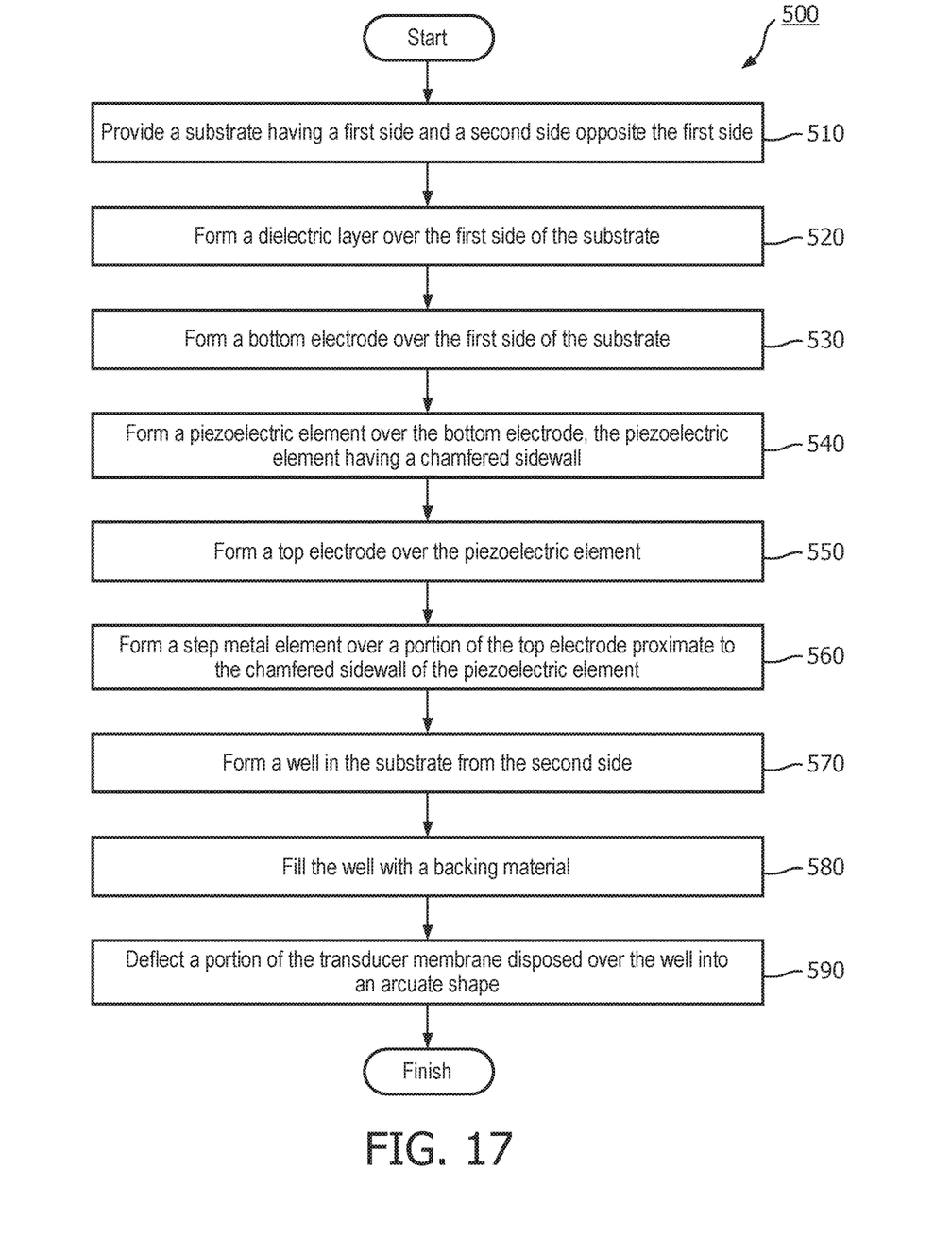
FIG. 17 is a flowchart of a method of fabricating a transducer according to various aspects of the present disclosure.

FIG. 17 is a flowchart of a method 500 for fabricating an ultrasound transducer according to various aspects of the present disclosure. The method includes a step 510, in which a substrate is provided. The substrate has a first side and a second side opposite the first side. In some embodiments, the substrate contains silicon.

The method 500 includes a step 520, in which a dielectric layer is formed over the first side of the substrate. In some embodiments, the dielectric layer may include silicon oxide, silicon nitride, or silicon oxynitride.

The method 500 includes a step 530, in which a bottom electrode is formed over the entire surface of the substrate. The bottom electrode may contain metal or multiple metals material, such as Titanium, Chromium, Gold, Aluminum, or combinations thereof. The bottom electrode may be patterned.

The method 500 includes a step 540, in which a piezoelectric element is formed over the bottom electrode. The piezoelectric element has a chamfered sidewall. In some embodiments, the piezoelectric element contains polyvinylidene fluoride (PVDF), polyvinylidene fluoride-trifluoroethylene (PVDF-TrFE), polyvinylidene fluoride-tetrafluoroethlene (PVDF-TFE), or sol-gel formed piezoelectric materials.

The method 500 includes a step 550, in which a top electrode is formed over the piezoelectric element. The top electrode may contain metal or multiple metals material, such as Titanium, Chromium, Gold, Aluminum, or combinations thereof In some embodiments, the top electrode is formed to include: a top segment disposed over a top surface of the piezoelectric element; a bottom segment disposed over the substrate, the bottom segment being non-planar with the top segment; and a via coupling the top segment to the bottom segment. The via may be disposed directly on the bottom segment. The via may include a recessed portion of the top electrode.

The method 500 includes a step 560, in which a step metal element is formed over a portion of the top electrode on the chamfered sidewall of the piezoelectric element. The step metal element and the top electrode have substantially similar material compositions.

The method 500 includes a step 570, in which a well is formed in the substrate from the second side. The well may be formed by an etching process. In some embodiments, the well is formed so that the etching stops at the dielectric layer. In other embodiments, the well is formed so that the dielectric layer is also etched, and the etching stops at the bottom surface of the substrate.

The method 500 includes a step 580, in which the well is filled with a backing material. In some embodiments, the backing material includes an epoxy material.

The method 500 includes a step 590, in which the top electrode, the piezoelectric element, and the bottom electrode—collectively constituting a transducer membrane—is deflected so that a portion of the transducer membrane disposed over the well has an arcuate shape.

It is understood that some of the steps discussed above may be performed in different sequences. It is also understood that additional fabrication steps may be performed to complete the fabrication of the transducer. However, these additional fabrication steps are not discussed herein for reasons of simplicity.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An imaging catheter, the catheter comprising
an elongate body comprising a distal portion;
an imaging core associated with the distal portion of the elongate body, the imaging core comprising at least one imaging assembly that includes:
at least one transducer element defining at least two surfaces and a sidewall;
a first electrode interfacing a first surface of the transducer element;
a second electrode interfacing a second surface and the sidewall of the transducer element;
a conductive material interfacing the second electrode and the side wall of the transducer element.

2. The imaging catheter of claim 1, wherein the transducer element is a piezoelectric film.

3. The imaging catheter of claim 1, wherein the first and second surfaces are opposing each other.

4. The imaging catheter of claim 1, wherein the first electrode further interfaces a substrate.

5. The imaging catheter of claim 4, further comprising a dielectric layer disposed between the first electrode and the substrate.

6. The imaging catheter of claim 1, wherein the conductive material and the second electrode comprises substantially similar material compositions.

7. The imaging catheter of claim 1, wherein the imaging catheter further comprises a rotatable shaft disposed within the elongate body, and the imaging assembly is positioned on a distal portion of the rotatable shaft.

8. The imaging catheter of claim 1, wherein the at least one transducer element forms a membrane.

9. The imaging catheter of claim 1, wherein the second electrode comprises a plurality of segments and a via through the segments.

10. The imaging catheter of claim 1, wherein the imaging core comprises a plurality of imaging assembly to form an array.

11. The imaging catheter of claim 1, wherein the substrate comprises a well.

12. The imaging catheter of claim 11, wherein the substrate comprises a front surface and a back surface opposite the front surface, and the well extends from the back surface of the substrate to, but not beyond, the front surface of the substrate.

13. The imaging catheter of claim 12, wherein the well is at least partially filled with a backing material.

* * * * *